United States Patent [19]

Meyer

[11] Patent Number: 5,730,592
[45] Date of Patent: Mar. 24, 1998

[54] DENTAL MATRIX FOR ELONGATED TOOTH CAVITIES HAS BOTTOM APRON FOR IMPROVED ADAPTATION

[76] Inventor: Alvin Meyer, 20 N. San Mateo Dr., San Mateo, Calif. 94401

[21] Appl. No.: 756,283

[22] Filed: Nov. 25, 1996

Related U.S. Application Data

[63] Continuation-in-part of Ser. No. 676,488, Jul. 8, 1996.

[51] Int. Cl.$^6$ ...................................................... A61C 5/04
[52] U.S. Cl. ........................................................ 433/39
[58] Field of Search ........................................ 433/39, 155

[56] References Cited

U.S. PATENT DOCUMENTS

| | | | |
|---|---|---|---|
| 844,079 | 2/1907 | Armstrong | 433/39 |
| 1,182,376 | 5/1916 | Ivory | 433/39 |
| 1,669,231 | 5/1928 | Curran | 433/39 |
| 2,267,836 | 12/1941 | Parkin | 433/39 |
| 2,567,101 | 9/1951 | Carpenter | 433/39 |
| 4,553,937 | 11/1985 | Ropers | 433/39 |

FOREIGN PATENT DOCUMENTS 3014278 11/1980 Germany ................ 433/39

*Primary Examiner*—Cary E. O'Connor

[57] ABSTRACT

A dental matrix or band applicable around a tooth or portion of a tooth undergoing a restoration of a cavity (17) to control the shape of the restorative material. The matrix is made of a thin strip of metal and features a bulbous concavity in its middle portion to simulate the contours normal to a tooth, a malleable apron (13, 23) which expedites its adaptation to the irregular contours of a tooth root, notches on the edges of the apron to permit control of the shape at all edges, and extending wings to facilitate wrapping of the matrix around a tooth being restored. The central portion of the matrix is malleable to permit it to be manipulated or shaped by the dentist to perfect its shape, while the wings are hardened to increase the force of the embrace of the matrix.

19 Claims, 1 Drawing Sheet

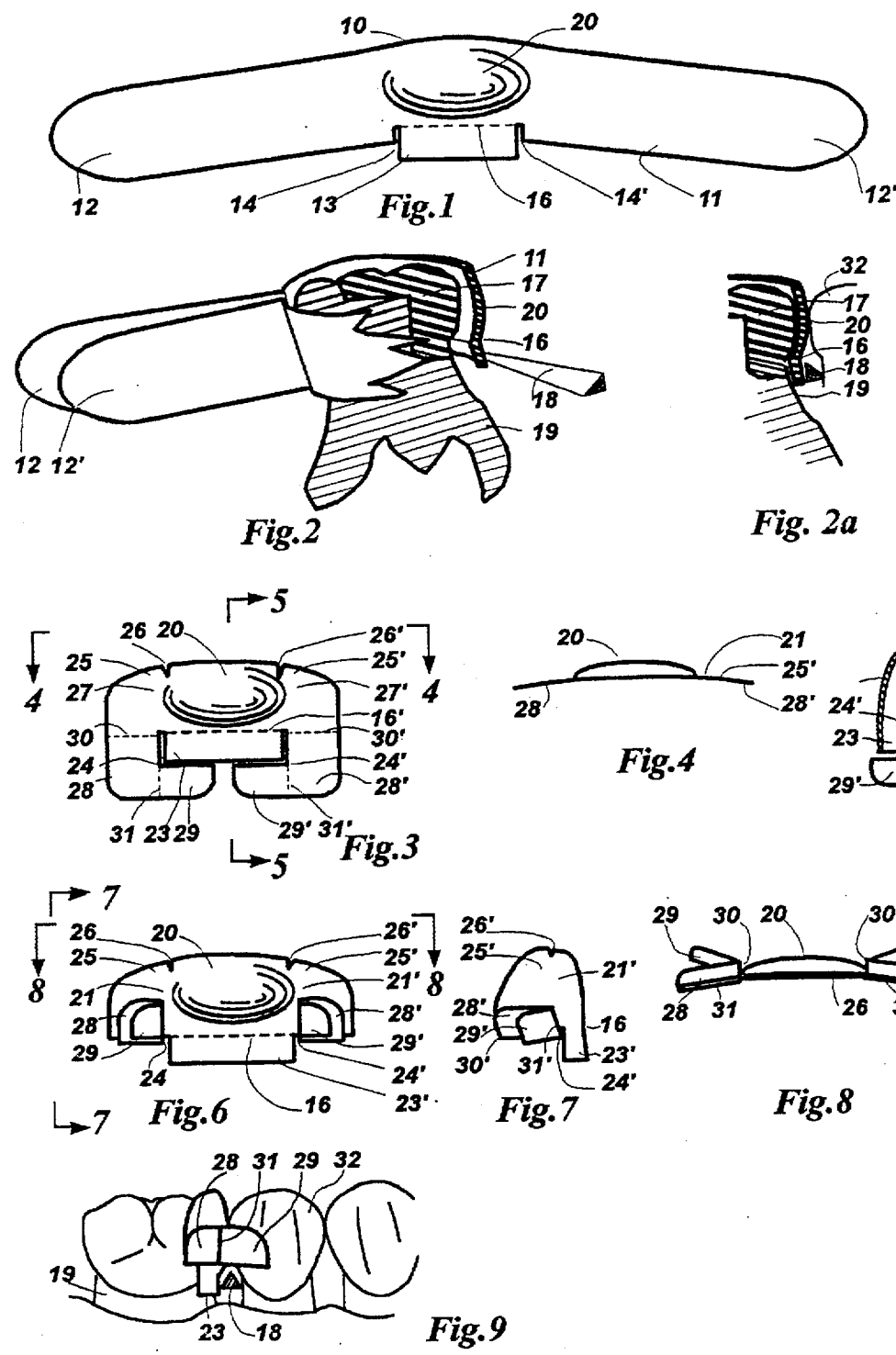

DENTAL MATRIX FOR ELONGATED TOOTH CAVITIES HAS BOTTOM APRON FOR IMPROVED ADAPTATION

CROSS-REFERENCE TO RELATED APPLICATION

This is a continuation in part of my application, U.S. Ser. No. 08/676,488, filed Jul. 8, 1996 pending.

FIELD OF INVENTION

This invention relates to dentistry, specifically to a form to contain and shape newly applied restorative materials within a tooth cavity, and more specifically to contain elongated restorations which extend through the tooth's crown and into its root.

PRIOR ART

Dentists commonly clean damaged tissues from a decayed tooth and refill the cavity with viscous materials (restoratives or fillings) which solidify within the cavity. In their viscous condition the restoratives will not hold their form and will sag due to gravity. Dentists have met this problem by wrapping a thin band, usually steel, around the prepared tooth to provide a temporary form or matrix to hold the restorative in a controlled shape until it solidifies.

It is well known that a filling which does not accurately reproduce the tooth's natural anatomy will engender a pathologic response from the surrounding tissues. In the interest of providing healthful services, dentists must fill or restore the tooth in a way which reproduces the natural anatomy precisely.

Various types of matrix forming shims have been used and described to aid in shaping the matrix to the tooth's natural anatomy. As examples, U.S. Pat. No. 1,255,109 to Russ (1918) describes a matrix band comprising a strip of metal having a transverse slot at one of its ends and lateral flanges which may be folded over the edges of the band. U.S. Pat. No. 2,310,448 to Lieb (1940) discloses a narrow thermoplastic ribbon exhibiting indentations described as useful for wrapping around the tooth. U.S. Pat. No. 2,594,367 to Tofflemire (1950) describes a girdling ribbon with an aperture through which a restorative may be injected into the encompassed tooth cavity. U.S. Pat. No. 3,411,214 to Lazarus (1968) shows of a dental band with a flattened metal loop embracing the body of the band. U.S. Pat. No. 5,330,353 to Wavrin (1994) discloses a dental matrix comprising a plastic member attached to a metal member. U.S. Pat. No. 5,380,198 to Suhonen (1995) describes a dental matrix comprising a metallic veneer layered over a transparent material.

My above copending application discloses a matrix shim which exhibits an apron, a bulbous contour, and edge notches which can also serve on the more complex embodiments shown in this application.

The foregoing designs have numerous deficiencies. They are cylindrical or conical and encircle the treated tooth. Dentists most commonly use a die-cut, symmetrical flat band in the shape of a small boomerang, i.e., it forms an obtuse angle. They often use external devices (vises or clamps) to clamp the two free ends of the band to form a loop which may be placed around the tooth. The vise has other controls to permit the diameter of the loop to be adjusted. When looped, such matrices form a conical segment which has the straight profile of a cone, instead of the freely flowing natural curves of a healthy tooth.

When the vise constricts a conical matrix to adapt it to the circumference of the narrowest tooth part, it will also reduce the circumference of the broader parts of the conical matrix, causing deficiencies in the contact between the tooth being restored and the neighboring teeth. As is well known, dentists desire such contact to exist for the reasons stated infra.

The constricting pressures of the band will bend the remaining fragments of a natural tooth to produce distortions during the filling process. Also, the stressed tissues rebound when the band is removed, generating potential voids at the interfaces. Further, a conical matrix, upon being drawn into a tighter loop against the inclined planes of the crown or upper part of the tooth (adjacent its biting surface), will tend to slide its thin, potentially incisive, edge toward the root and risk injury to healthy adjacent tissues.

The contours of the matrix of the Lieb patent are specific for the front twelve teeth (the anteriors), and will not shape posterior fillings appropriately.

Another problem which is not solved by prior-art matrices occurs because diseases or genetic influences sometimes cause a diminution of a tooth's gum and bone tissues, such that a portion of its root may be exposed to decay. Root decays often require fillings extending from the biting surfaces across the tooth's neck and into the damaged root. When a prepared cavity extends into the tooth's root, a conical form will deviate even further from a tooth's original contours because it does not accommodate the anatomical diversity which is normal at the crown-to-tooth junction, commonly referred to as the cervix or neck. Roots will be irregularly cylindrical while the crown will be seen as a truncated cone which is attached at its apex to the root's cylinder. The juncture of unlike forms produces a beltline, the cervix, which cannot be reproduced with matrices with straight profiles.

OBJECTS AND ADVANTAGES

Accordingly several objects and advantages of the present invention are:

(1) to provide an improved dental matrix;
(2) to provide a dental matrix which can be accurately and quickly adapted to the conformations of a tooth crown and its root with a single application;
(3) to provide such a matrix which will reproduce the natural constriction of a tooth's cervical anatomy;
(4) to provide a matrix which can be inserted, adapted and retained with instruments readily available in dental clinics; and
(5) to provide a matrix with minimal imposition upon the tissues not involved in the treatment.

Other objects and advantages are:

(6) to provide a matrix which may be more perfectly adapted by pressing with hand-held instruments to generate more precisely controlled contours;
(7) to provide a matrix with outlines that can be shortened for more precise adaptation using hand-held shears;
(8) to provide a matrix form which may be rapidly and inexpensively die-cut and shaped from sheet stock;
(9) to provide a matrix which will function in commonly used constricting vises which will facilitate the control of an anatomically correct cervix;
(10) to provide a matrix which sustain its position without an external device;
(11) to provide a matrix which can be made of commercially available alloys and plastics in thicknesses likely to be advantageous;

(12) to provide a matrix which will not be adversely modified by solutions and equipment commonly used to produce sterility, and

(13) to provide a matrix which is reusable.

Further objects and advantages will become apparent from a consideration of the ensuing description and drawings.

DRAWING FIGURES

FIG. 1 shows a view of an encircling long matrix in a die-cut form in accordance with the invention.

FIG. 2 shows a section of a cavity-bearing tooth with the matrix looped around it.

FIG. 2a is a view of the looped band drawn tightly and wedged.

FIG. 3 is a plan view of a standalone matrix in accordance with the invention.

FIG. 4 is a sectional view of the standalone matrix seen at plane 4—4 of FIG. 3.

FIG. 5 is an edge view of the standalone matrix as seen from plane 5—5 of FIG. 3.

FIG. 6 is a plan view of the standalone matrix with its wings folded twice.

FIG. 7 is a lateral view of the standalone matrix as seen from plane 7—7 of FIG. 6. The matrix has been rolled to conform to the tooth's curvature.

FIG. 8 is an edge view as seen from plane 8—8 of FIG. 6.

FIG. 9 is a lateral view of the standalone matrix in a tooth's arch.

Reference Numerals

| | |
|---|---|
| 10 | midsection of matrix |
| 12 & 12' | extensions or wings |
| 13 | apron for root surface cavity |
| 14 & 14' | sheared slits |
| 16 | fold line at beltline |
| 17 | section of tooth cavity |
| 18 | wedge for pressing apron to root |
| 19 | section of tooth root |
| 20 | bulbous contour |
| 21 | body of standalone shim |
| 23 | apron |
| 24 & 24' | slits which permit independent movement |
| 25 & 25' | lateral limits of spherical bulge |
| 26 & 26' | edge separations or sheared slits |
| 27, 27' | short wing |
| 28 & 28' | vertical wing extensions |
| 29 & 29' | horizontal wing extensions |
| 30 & 30' | crease of horizontal fold |
| 31 & 31' | crease of vertical fold |
| 32 | abutment tooth |

Description—FIG. 1—Vise-Tightened Matrix

FIG. 1 shows a dental matrix in accordance with a preferred embodiment of the invention. It comprises an elongated strip forming an angle at its middle zone or midsection 10. Two flat wings or extensions 12 and 12' extend from midsection 10 and form an obtuse angle. Each wing terminates in a semicircular end. Wings 12 and 12' are essentially flat and flexible until they are rolled to encircle the tooth. The upper edge of the midsection is arcuate. The upper portion of the midsection, below the upper edge, has a concave indentation 20 to more closely simulate the bulbous anatomy of a tooth's crown.

Extending downward from the lower edge of midsection 10 is an essentially rectangular and flat apron 13. The upper margin of apron 13 (indicated by broken line 16) is continuous with the rest of the matrix so that the entire matrix is homogeneous. The upper portions of the sides of apron 13 are separated from the rest of the matrix by lateral separations or slots 14 and 14'. Margin 16 thus extends from the upper termination of separation 14 to the upper termination of separation 14'. Margin 16 is scored or minutely folded to form a hinge or bendable line.

Although the matrix may be formed of many substances, including metals, elastomers, and various plastics, preferably it is die cut and formed of stainless steel, most suitably Formula 304 stainless steel (American Iron and Steel Institute). Preferably it is about 40 to 50 microns thick, about 8 centimeters wide overall, and about 1 centimeter tall overall. Its wings are about 6 millimeters tall and about 3 centimeters wide.

Operation—FIG. 2

Assume that the lateral surface of a tooth 19 (FIG. 2) has been damaged by decay so that it has an elongated carious area or cavity 17 which extends down to the tooth's root. The area is first cleaned and shaped by drilling and milling in a well-known manner.

The matrix of FIG. 1 is then bent or rolled so that one wing 12 lies against its counterpart 12'. This forms a bight or loop portion at midsection 10. Overlapping wings 12 and 12' are clasped by a known external device or vise (not shown) capable of pinching the two wings together and then capable of drawing the wings through a small sleeve (not shown) to a reduced the loop size and thereby encircle the tooth. The assembly is sterilized and tested in position around prepared tooth cavity 17. After any necessary adjustments are made, the dentist then tightens the vise to pull wings 12 and 12' to constrict the loop tightly around the cervix or neck of the tooth, and, in the best of circumstances, loosely around the tooth's most bulbous zone.

Apron 13 covers a portion of the root of tooth 19 to seal this portion of the cavity against leakage. Margin 16 and separations 14 and 14' enable the dentist to adapt the apron to the irregularities of the root and incline midsection 10 of the matrix to contact an abutting tooth 32 (FIG. 2a). When the midsection contacts an adjacent or abutting tooth, it will be able to shape the restoration so that it will contact the adjacent tooth (not shown). As is well known, dentists desire adjacent teeth to contact each other to preclude packing of food particles between adjacent teeth and unnatural drifting of the teeth.

Concave indentation 20 allows the point which contacts the adjacent tooth to be positioned properly. When the matrix is well positioned, the dentist inserts an elongated tapered member 18 (wedge) with a triangular cross section horizontally between the outside of the matrix and the adjacent tooth 32 (see FIG. 9) to cause apron 13 to press against the root surface of tooth 19.

Then a viscous prosthetic material, restorative, or filling is placed in the cavity between the tooth and the matrix. Suitable materials are gold, a silver/mercury amalgam, mixtures of plastics and inorganic fillers (composites), or other materials well known and used in dental arts which harden shortly after insertion into cavity 17. The matrix holds the filling in the general shape or anatomical configuration of the original tooth (before the cavity existed) and prevents it from slumping so that it will harden in the desired shape. The apron affords control over the repair of root 19 and enables it to be restored to its original configuration while permitting additional controls for the restoration of crown 17, even though the two surfaces diverge.

Then the dentist removes the matrix and shapes the filling to the anatomy of the original tooth.

Description—FIGS. 3 to 9—Standalone Matrix

FIG. 3 shows a standalone matrix, i.e., one which is not clamped around a tooth, but instead is inserted between the tooth to be filled and an adjacent tooth. Such a matrix also forms a mold around the cavity of the tooth to be treated. Dentists use it when they want to avoid the use of supplementary external support devices, save treatment time, and/ or feel the use of such devices will adversely affect adjacent conditions.

The matrix of FIG. 3 has the same bulbous concavity 20 as that of FIG. 1, but has short wings 27 and 27' that can be bent, twisted, or rolled to develop an active contact with an adjacent tooth. This matrix is generally rectangular and about one centimeter tall and two centimeters wide. The upper edge is slightly convex-arcuate and has two edge separations or notches 26 and 26'. The lower portion is sheared to provide L-shaped shear slots or separations 24 and 24' to form a rectangular apron 23 which is free on three of its edges and homogeneously attached to the rest of the matrix at margin 16' on its fourth side. Wings 27 and 27' extend laterally from the central portion and have two vertical, downwardly extending extensions 28 and 28'. Two horizontal extensions 29 and 29' extend laterally inward from extensions 28 and 28' and approach the midline of the matrix. Extensions 28 and 28' are delineated from the rest of the respective by horizontal score lines 30 and 30' which are collinear with margin 16'. Extensions 29 and 29' are delineated from extensions 28 and 28' by light scored lines 31 and 31'.

All parts of the wings are pressure hardened during the cutting process, while the midsection remains annealed and hence more malleable. This is accomplished by working the lateral surfaces of the ribbon stock before it is fed to the cutting die to work harden them. (The ribbon stock should not be work hardened by pounding, but rather by rolling, stamping, drawing, or otherwise stressing it.)

FIG. 4 is a view of the matrix seen from plane 4—4' of FIG. 3. Notice bulbous midsection 20 and wings 27 and 27'.

The matrix is hand rolled horizontally to an incomplete cylinder. FIG. 5 shows a sectional view taken at plane 5—5 of FIG. 3 after such rolling.

Next the dentist folds wing extensions 28 and 28' upward at crease lines 30 and 31' toward the flat surfaces of the upper portions of wings 27 and 27'. The dentist folds wing extensions 29 and 29' outward along crease lines 31 and 31' to form a partially opened accordion fold. FIG. 6 is a view of the underside of the matrix of FIG. 3 after such folding. Here bulbous cavity 20 is seen as a convexity.

FIG. 7 is an edge view as seen from plane 7—7' of FIG. 6 with wing 29 folded horizontally at line 31 and wing 28 folded vertically upward at line 30 to form a partially opened accordion fold. The dentist had rolled the matrix to match the tooth's curvature.

FIG. 8 is an edge view of the matrix with wing extensions 28 and 28' and wing extensions 29 and 29' partially folded as seen from plane 8—8 of FIG. 6.

The dentist then inserts the matrix (FIG. 9) in the arch or space between two teeth. FIG. 9 is a lateral view of the arch with the matrix inserted. The dentist then inserts a wedge 18 to press apron 23 firmly against root surface 19. The dentist has adjusted the angles at lines 30 and 30' and lines 31 and 31' to generate lateral pressures against adjacent tooth 32. Finally, the dentist has also hand adjusted bulbous curvature 20 to properly meet adjacent tooth 32.

Description—Operation—FIG. 9

The dentist prepares the standalone design for use by rolling the matrix horizontally to simulate the tooth's curvature and then bending extensions 28 and 28' upwardly and the distal wing segments perpendicularly to create an accordion fold, as shown in FIGS. 6 through 9.

The dentist then inserts the accordion-folded matrix between two teeth. The dentist may make adjustments by pressing on the matrix or shearing. it to fit the contours of the tooth. Next the dentist wedges apron 23 by inserting a wedge 18 between abutment tooth 32 and apron 23 to pin the apron firmly against the residue of root 19. Then the dentist manually repositions accordion folded wings so that they press against the adjacent tooth. The dentist may apply numerous other patterns of twisting, spindling, and folding according to the spaces presented by various dental arches. Although FIG. 9 shows the cavity on the mesial surface (i.e., the surface situated toward the middle of the front of the jaw along the curve of the dental arch), the dentist may use the matrix to restore decayed surfaces on the opposite or distal surface, i.e., the surface which faces the back of the mouth.

FIG. 9 shows the matrix of FIG. 3 with its wings folded as shown in FIG. 6 and positioned in the arch adjacent to the tooth being restored. The dentist has finger rolled it to a horizontal are (as in FIGS. 5 and 7) to simulate the circumference of the tooth and has positioned it in the space adjacent the cavity under treatment and has wedged it in at the root level. The dentist has opened crease 31 to a more obtuse angle to cause wing 29 to generate pressure against the abutment tooth.

Edge separations 26 and 26' enable the dentist to adjust the free edge of the matrix and fold of the flee edge of the matrix toward the middle axis of the tooth (not shown) to recreate the rolling contour natural for the proximal surface of the tooth.

When the restorative material has hardened, the dentist removes and sterilizes the matrix for reuse.

SUMMARY, RAMIFICATIONS, AND SCOPE

Accordingly, the reader will see that the dentist may advantageously use the adjustable apron of the matrix, together with known instruments and methods, to temporarily provide a more accurate retaining wall while the filling material hardens. The apron provides particular advantages when the decay has extended beyond the crown and into the root tissues, a circumstance which imposes additional requirements for control upon the dentist.

While its principal usage will be in the treatment of carious lesions in teeth with exposed roots, the apron affords additional control in many applications where the root may be exposed but not carious. Because a matrix loop encircles a somewhat conical tooth, the constricting tension supplied by the vise may develop a force vector which threatens the gums and root surfaces by directing the thin edge of the matrix toward the narrowest diameter, the root-to-tooth junction. The wider surface contact and more intimate adaptation provided by an apron will distribute the closing forces to a broader area of the tooth root, provide additional space for a wedge and afford greater frictional resistance to any dislodging movement. Fold 16 of apron 13 or 23 presents a blunt contact zone to the root.

While the above description contains many specificities, the reader should not construe these as limitations on the scope of the invention, but as exemplifications of the presently preferred embodiment thereof. Those skilled in the art will envision many other ramifications and variations within the teachings of the invention. For example, the dentist may incline the assembled loop or standalone matrix to or from the central axis of a tooth after he or she has wedged the apron so that the restored tooth and root planes are properly aligned for functioning with its abutment tooth. Separations 26 and 26' will ease the shaping of the proximal space to facilitate the application of cleansing instruments. In lieu of a homogeneous matrix, it may be formed of separate parts which are welded or attached together.

Thus the reader should determine the scope of the invention by the appended claims and their legal equivalents, and not by the examples given.

I claim:

1. A dental matrix band for use by dentists to aid in restoring a decayed tooth area, comprising:
    an elongated flexible band having a midsection with a bottom and a pair of opposing sides,
    a pair of wings extending laterally from said sides of said midsection, respectively, and
    an apron extending from said bottom of said midsection, said apron comprising a portion of flexible material having a pair of opposing sides separate from the rest of said matrix
    said pair of wings being harder and less malleable than said midsection.

2. The dental matrix of claim 1 wherein said wings are work hardened.

3. A standalone dental matrix band for use by dentists to aid in restoring a decayed tooth area, comprising:
    a flexible sheet having a midsection having a bottom and a pair of opposing sides,
    an apron extending from said bottom of said midsection, said apron comprising a portion of flexible material having a pair of opposing sides separate from the rest of said flexible sheet,
    a pair of wings extending laterally from said sides of said midsection, respectively,
    a pair of vertical extensions extending down from said pair of wings, respectively, and
    a pair of horizontal extensions extending inward toward each other from said pair of vertical extensions, respectively.

4. The standalone dental matrix of claim 3 wherein said band is made of metal and said midsection, said pair of wings, and said apron are integral and homogeneous.

5. The standalone dental matrix of claim 3 wherein said flexible sheet is made of stainless steel.

6. The dental matrix of claim 3 wherein said pair of vertical extensions are separated from said apron by a pair of respective vertical separations.

7. The dental matrix of claim 6 wherein said apron has a lower edge which is perpendicular to and between said two vertical separations.

8. The dental matrix of claim 3 wherein said pair of horizontal extensions are separated from said apron by a pair of respective horizontal slots.

9. The dental matrix of claim 8 wherein said horizontal extensions are below a lower edge of said apron.

10. The dental matrix of claim 3 wherein said flexible sheet has an upper edge with a plurality of separations.

11. The dental matrix of claim 3 wherein said pair of wings are harder and less malleable than said midsection.

12. The dental matrix of claim 11 wherein said wings are work hardened.

13. A method of using a dental matrix to aid in restoring a decayed tooth area, comprising:
    providing an elongated flexible band having a midsection, a bottom, and a pair of opposing sides,
    providing said band with a pair of wings extending laterally from said opposing sides of said midsection, respectively, said band and said wings having an outline, and
    providing an apron extending from said bottom of said midsection, said apron being made of a flexible material having a pair of opposing sides, said sides having upper portions respectively separated from the rest of said elongated flexible band by a pair of spaced-apart slits, a lower portion of said apron projecting down beyond said outline of said band and said wings, said apron being joined to said bottom of said midsection by a defined bendable hinge line so that said apron can be bent along said hinge line with respect to said midsection to adapt itself more conformingly to a tooth's lower contours, and
    applying said matrix to a tooth by wrapping said band with said pair of wings around said tooth so that said band and said wings surround an upper portion of said tooth and said apron extends from said midsection and bends outwardly from said tooth along said hinge line such that said apron covers a bottom portion of said tooth and a contiguous root surface adjacent said tooth, yet said band will not be distorted.

14. The method of claim 13 wherein said band is made of metal and said midsection, said pair of wings, and said apron are integral and homogeneous.

15. The method of claim 13 wherein said band is made of stainless steel.

16. A method of using a dental matrix band to aid in restoring a decayed tooth area, comprising:
    providing an elongated flexible band having a midsection with a bottom and a pair of opposing sides,
    providing said band with a pair of wings extending laterally from said sides of said midsection, respectively, and
    providing an apron extending down from said bottom of said midsection, said apron being made of a flexible material having a pair of opposing sides separate from the rest of said matrix, each of said opposing sides of said apron having an upper portion adjacent said bottom of said midsection, each upper portion being separated from the rest of said elongated flexible band by a separation or slit, so as to provide two separations or slits, said two separations or slits being substantially parallel and spaced apart from each other, said apron being joined to said midsection by a hinge line,
    applying said matrix to a tooth by wrapping said band with said pair of wings around said tooth so that said band and said wings surround an upper portion of said tooth and said apron extends from said midsection and bends outwardly from said tooth along said hinge line such that said apron covers a bottom portion of said tooth and a contiguous root surface adjacent said tooth, yet said band will not be distorted.

17. The method of claim 16 wherein said apron has a lower edge that is perpendicular to and between said two separations or slits.

18. The method of claim 16 wherein said apron has a lower edge that protrudes beyond the outline of the rest of said matrix.

19. The method of claim 16 wherein said elongated flexible band has an upper edge with a plurality of separations.

* * * * *